(12) United States Patent
Kobayashi et al.

(10) Patent No.: US 9,370,182 B2
(45) Date of Patent: Jun. 21, 2016

(54) ANTIMICROBIAL PEPTIDE AND USE THEREOF

(71) Applicant: TOAGOSEI CO., LTD., Tokyo (JP)

(72) Inventors: Nahoko Kobayashi, Tsukuba (JP); Tetsuhiko Yoshida, Tsukuba (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 14/397,920

(22) PCT Filed: May 23, 2013

(86) PCT No.: PCT/JP2013/064393
§ 371 (c)(1),
(2) Date: Oct. 30, 2014

(87) PCT Pub. No.: WO2013/180011
PCT Pub. Date: Dec. 5, 2013

(65) Prior Publication Data
US 2015/0126434 A1 May 7, 2015

(30) Foreign Application Priority Data
May 28, 2012 (JP) ................... 2012-121256

(51) Int. Cl.
| | | |
|---|---|---|
| A61K 38/16 | (2006.01) | |
| C07K 14/00 | (2006.01) | |
| A61P 31/00 | (2006.01) | |
| A01N 43/38 | (2006.01) | |
| C07K 14/705 | (2006.01) | |
| A01N 43/36 | (2006.01) | |
| C07K 7/08 | (2006.01) | |
| C07K 14/47 | (2006.01) | |
| A01N 37/46 | (2006.01) | |
| A61K 38/00 | (2006.01) | |

(52) U.S. Cl.
CPC ............... *A01N 43/38* (2013.01); *A01N 37/46* (2013.01); *A01N 43/36* (2013.01); *C07K 7/08* (2013.01); *C07K 14/00* (2013.01); *C07K 14/4723* (2013.01); *C07K 14/705* (2013.01); *C07K 14/70503* (2013.01); *C07K 14/70546* (2013.01); *C07K 14/70596* (2013.01); *A61K 38/00* (2013.01)

(58) Field of Classification Search
CPC .............. A61K 38/00; C07K 14/705; C07K 14/70503; C07K 14/70546; C07K 14/70596; C07K 7/08; C07K 14/00; C07K 14/4723; A01N 37/46; A01N 43/36; A01N 43/38
See application file for complete search history.

(56) References Cited

U.S. PATENT DOCUMENTS

| | | | |
|---|---|---|---|
| 4,578,269 A | 3/1986 | Morein | |
| 4,744,983 A | 5/1988 | Morein | |
| 4,867,975 A | 9/1989 | Gelb, Jr. | |
| 4,981,684 A | 1/1991 | MacKenzie et al. | |
| 5,178,860 A | 1/1993 | MacKenzie et al. | |
| 5,242,932 A | 9/1993 | Gandy et al. | |
| 5,441,931 A * | 8/1995 | Sprecher | C07K 14/81 435/212 |
| 5,519,003 A | 5/1996 | Mochly-Rosen et al. | |
| 5,679,355 A | 10/1997 | Alexander et al. | |
| 5,961,970 A | 10/1999 | Lowell et al. | |
| 6,037,521 A | 3/2000 | Sato et al. | |
| 6,333,167 B1 | 12/2001 | Quinet et al. | |
| 6,340,583 B1 | 1/2002 | Yan et al. | |
| 6,403,353 B1 | 6/2002 | Yan et al. | |
| 6,423,684 B1 | 7/2002 | Mochly-Rosen et al. | |
| 6,476,189 B1 | 11/2002 | Yamakawa et al. | |
| 8,822,408 B2 | 9/2014 | Yoshida et al. | |
| 2003/0125242 A1 | 7/2003 | Rosenecker et al. | |
| 2003/0166215 A1 | 9/2003 | Yan et al. | |
| 2003/0229202 A1 | 12/2003 | Guo et al. | |
| 2004/0175751 A1 | 9/2004 | Yan et al. | |
| 2004/0186052 A1 | 9/2004 | Iyer et al. | |
| 2004/0226056 A1 | 11/2004 | Roch et al. | |
| 2005/0129701 A1 | 6/2005 | Marasco et al. | |
| 2006/0057668 A1 | 3/2006 | Yoshida et al. | |
| 2006/0100134 A1 | 5/2006 | Guo et al. | |
| 2006/0166917 A1 | 7/2006 | Lindeman et al. | |
| 2006/0270834 A1 | 11/2006 | Kanno | |
| 2007/0065941 A1 | 3/2007 | Kondo et al. | |
| 2008/0076145 A1 | 3/2008 | Cummings et al. | |
| 2009/0004144 A1 | 1/2009 | Tabira et al. | |

(Continued)

FOREIGN PATENT DOCUMENTS

| | | |
|---|---|---|
| EP | 0 653 154 A2 | 5/1995 |
| EP | 1 634 956 A1 | 3/2006 |

(Continued)

OTHER PUBLICATIONS

Water, from http://www.biology-online.org/dictionary/Water, pp. 1-3, accessed Apr. 24, 2014.*
DMSO—The Source Natural Foods, from http://www.thesourcenatural.com/...isplayMonograph.asp?storeID=dhap6v4fb7sr2nm700akhlbd3cmfbxmd&DocID=bottomline-dimethylsulfoxide, pp. 1-7, accessed Sep. 23, 2015.*
Feb. 22, 2013 Office Action issued in U.S. Appl. No. 13/386,539.
Feb. 22, 2013 Office Action issued in U.S. Appl. No. 13/386,582.
Apr. 17, 2013 Office Action issued in U.S. Appl. No. 13/503,220.

(Continued)

*Primary Examiner* — Julie Ha
*Assistant Examiner* — Li Ni Komatsu
(74) *Attorney, Agent, or Firm* — Oliff PLC

(57) ABSTRACT

A composition including an artificially synthesized antimicrobial peptide that is not present as a mature peptide in nature. The composition includes an artificially synthesized peptide that has an antimicrobial activity against at least one strain of bacteria or fungi and includes an amino acid sequence represented by any one of SEQ ID NOs: 1 to 6 or an amino acid sequence formed by substituting, deleting and/or adding one, two or three amino acid residues in/from/to the amino acid sequence, and further including at least one species of pharmaceutically acceptable carrier.

3 Claims, No Drawings

(56) References Cited

U.S. PATENT DOCUMENTS

| | | |
|---|---|---|
| 2009/0253618 A1 | 10/2009 | Kanno et al. |
| 2010/0074925 A1 | 3/2010 | Carmon |
| 2010/0093059 A1 | 4/2010 | Wolff et al. |
| 2010/0169988 A1 | 7/2010 | Kohli et al. |
| 2010/0209490 A1 | 8/2010 | Morita et al. |
| 2010/0297758 A1 | 11/2010 | Yoshida et al. |
| 2011/0229912 A1 | 9/2011 | Cai et al. |
| 2011/0269942 A1 | 11/2011 | Morita et al. |
| 2012/0035112 A1 | 2/2012 | Yoshida et al. |
| 2012/0122210 A1 | 5/2012 | Yoshida et al. |
| 2012/0122225 A1 | 5/2012 | Kobayashi et al. |
| 2012/0208752 A1 | 8/2012 | Yoshida et al. |
| 2013/0005034 A1 | 1/2013 | Yoshida et al. |
| 2013/0079273 A1 | 3/2013 | Yoshida et al. |
| 2013/0345408 A1 | 12/2013 | Fukushima et al. |
| 2014/0072592 A1 | 3/2014 | Okamoto et al. |
| 2014/0178990 A1 | 6/2014 | Yoshida et al. |
| 2014/0335613 A1 | 11/2014 | Yoshida et al. |
| 2015/0273018 A1 | 10/2015 | Kobayashi et al. |

FOREIGN PATENT DOCUMENTS

| | | |
|---|---|---|
| EP | 1 918 297 A1 | 5/2008 |
| JP | 59-186921 A | 10/1984 |
| JP | 07-132033 A | 5/1995 |
| JP | 07-505389 A | 6/1995 |
| JP | 09-323928 A | 12/1997 |
| JP | 2000063400 A | 2/2000 |
| JP | 2001-199997 A | 7/2001 |
| JP | 2001186887 A | 7/2001 |
| JP | 2003-137899 A | 5/2003 |
| JP | 2004-357543 A | 12/2004 |
| JP | 2005-511047 A | 4/2005 |
| JP | 2005-154338 A | 6/2005 |
| JP | 2005-330206 A | 12/2005 |
| JP | 3854995 B2 | 12/2006 |
| JP | 2007-145761 A | 6/2007 |
| JP | 2007-159429 A | 6/2007 |
| JP | 2007-517057 A | 6/2007 |
| JP | 2009-209064 A | 9/2009 |
| JP | 2011-016763 A | 1/2011 |
| JP | 2012-518042 A | 8/2012 |
| WO | 95/21252 A2 | 8/1995 |
| WO | 02/18572 A2 | 3/2002 |
| WO | 02/077171 A2 | 10/2002 |
| WO | 03/048337 A2 | 6/2003 |
| WO | 03/076561 A2 | 9/2003 |
| WO | 03091429 A1 | 11/2003 |
| WO | 2004/056854 A1 | 7/2004 |
| WO | 2005/086800 A2 | 9/2005 |
| WO | 2007/010989 A1 | 1/2007 |
| WO | 2007/149293 A2 | 12/2007 |
| WO | 2008/008569 A2 | 1/2008 |
| WO | 2008/027017 A1 | 3/2008 |
| WO | 2008/035350 A1 | 3/2008 |
| WO | 2008/125360 A1 | 10/2008 |
| WO | 2009/020093 A1 | 2/2009 |
| WO | 2009/020094 A1 | 2/2009 |
| WO | 2009/047002 A2 | 4/2009 |
| WO | 2009/053696 A1 | 4/2009 |
| WO | 2009/093692 A1 | 7/2009 |
| WO | 2010/096470 A2 | 8/2010 |
| WO | 2010/117078 A1 | 10/2010 |
| WO | 2010117079 A1 | 10/2010 |
| WO | 2011/052679 A1 | 5/2011 |
| WO | 2011152524 A1 | 12/2011 |
| WO | 2012093706 A1 | 7/2012 |
| WO | 2012093732 A1 | 7/2012 |

OTHER PUBLICATIONS

Alexander et al., "The Role of Suppressors of Cytokine Signaling (SOCS) Proteins in Regulation of the Immune Response," Annu. Rev. Immunol., vol. 22, pp. 503-529, 2004.

Larsen et al., "Suppressors of Cytokine Signalling: SOCS," APMIS, vol. 110, pp. 833-844, 2002.

Jun. 18, 2013 Supplementary European Search Report issued in European Application No. 10 82 6811.

Dieterlen-Lievre, "On the Origin of Haemopoietic Stem Cells in the Avian Embryo: An Experimental Approach," J. Embryol. exp. Morph., vol. 33, No. 3, pp. 607-619, 1975.

Aug. 7, 2013 Office Action issued in U.S. Appl. No. 13/258,788.

Aug. 6, 2013 Office Action issued in U.S. Appl. No. 13/386,582.

Copani et al., "Mitotic Signaling by ?-amyloid Causes Neuronal Death," The FASEB Journal, vol. 13, pp. 2225-2234, Dec. 1999.

De Strooper et al., "Proteolytic Processing and Cell Biological Functions of the Amyloid Precursor Protein," Journal of Cell Science, vol. 113, pp. 1857-1870, 2000.

Zhang et al., "NSA2, A Novel Nucleolus Protein Regulates Cell Proliferation and Cell Cycle," Biochemical and Biophysical Research Communications, vol. 391, pp. 651-658, 2010.

Mar. 24, 2014 Office Action issued in European Application No. 10 826 811.1.

Apr. 22, 2014 Supplementary European Search Report issued in European Application No. 11 78 9925.2.

Neer et al., "The Ancient Regulatory-Protein Family of WD-Repeat Proteins," Nature, vol. 371, pp. 297-300, 1994.

Apr. 15, 2014 European Search Report issued in European Application No. 14153135.0.

Selkoe, "Normal and Abnormal Biology of the Beta-Amyloid Precursor Protein," Annu. Rev. Neurosci., vol. 17, pp. 489-517, 1994.

Hayashi et al., "Alzheimer Amyloid Protein Precursor Enhances Proliferation of Neural Stem Cells from Fetal Rat Brain," Biochemical and Biophysical Research Communications, vol. 205, No. 1, pp. 936-943, 1994.

Venkataramani et al., "Histone Deacetylase Inhibitor Valproic Acid Inhibits Cancer Cell Proliferation via Down-Regulation of the Alzheimer Amyloid Precursor Protein," The Journal of Biological Chemistry, vol. 285, No. 14, pp. 10678-10689, Apr. 2, 2010.

Kwak, "Studies on the Novel Function of Amyloid Precursor Protein in Glial Differentiation of Neural Stem Cells," Dissertation, pp. 1-173, 2006.

Jun. 25, 2013 Search Report issued in International Application No. PCT/JP2013/064393.

Soscia, Stephanie et al. "The Alzheimer's Disease-Associated Amyloid b-Protein Is an Antimicrobial Peptide". vol. 5, 1-10, 2010. PLoS ONE.

Martoglio, Bruno et al. "Signal sequences: more than just greasy peptides". vol. 8, 410-415, 1998, trends in Cell Biology.

Papareddy, Praveen et al. "Antimicrobial activity of peptides derived from human b-amyloid precursor protein". vol. 18, 183-191, 2012, Journal of Peptide Science.

Panegyres, Peter et al. "The Functions of the Amyloid Precursor Protein Gene and Its Derivative Peptides: I Molecular Biology and Metabolic Processing". vol. 2, 120-131, 2011, Neuroscience & Medicine.

Strooper, Bart et al. "Proteolytic processing and cell biological functions of the amyloid precursor protein". vol. 113, 1857-1870, 2000, Journal of Cell Science.

Dec. 2, 2014 International Preliminary Report on Patentability issued in International Application No. PCT/JP2013/064393.

Dec. 18, 2014 Notification of Reasons for Refusal issued in Japanese Application No. 2011-538478.

Cells—Merck Manual, from http://www.merckmanuals.com/home/fundamentals/ the_human_body/cells.html, pp. 1-2, accessed Dec. 24, 2014.

DNA and cell division, from http://www.bbc.co.uk/schools/gcsebitesize/science/ add_aqa/inheritance/dna_cell_division . . . , pp. 1-6, accessed Dec. 28, 2014.

O'Sullivan et al., "Cytokine Receptor Signaling Through the Jak-Stat-Socs Pathway in Disease," Molecular Immunology, vol. 44, pp. 2497-2506, 2007.

Stem cell information, from http://stemcells.nih.gov/StaticResources/info/ popups/glossary.html, pp. 1-6, accessed Dec. 23, 2014.

Woodbury et al., "Adult Rat and Human Bone Marrow Stromal Cells Differentiate Into Neurons," Journal of Neuroscience Research, vol. 61, pp. 364-370, 2000.

Jan. 23, 2015 Office Action issued in U.S. Appl. No. 14/163,371.

(56) References Cited

OTHER PUBLICATIONS

McKinnon et al., "Neurinflammation in Glaucoma," XIX Biennial Meeting of The International Society for Eye Research, Jul. 18-23, 2010, Montreal, Canada.
Luo et al., "Differential Functions of Tumor Necrosis Factor Receptor 1 and 2 Signaling in Ischemia-Mediated Arteriogenesis and Angiogenesis," The American Journal of Pathology, pp. 1886-1898, vol. 169, No. 5, Nov. 2006.
Nakazawa et al., "Tumor Necrosis Factor-? Mediates Photoreceptor Death in a Rodent model of Retinal Detachment," Investigative Opthamology & Visual Science, pp. 1384-1391, vol. 52, No. 3, Mar. 2011.
Clark et al., "Is TNF a Link between Aging-Related Reproductive Endocrine Dyscrasia and Alzheimer's Disease?" Journal of Alzheimer's Disease, pp. 691-699, vol. 27, 2011.
Sim et al., "Ligand-Dependent Activation of the Chimeric Tumor Necrosis Factor Receptor-Amyloid Precursor Protein (APP) Reveals Increased APP Processing and Suppressed Neuronal Differentiation," Neurosignals, pp. 9-23, vol. 18, 2010.
Nov. 12, 2013 International Search Report issued in International Application No. PCT/JP2013/078222.
Apr. 21, 2015 International Preliminary Report on Patentability issued in International Application No. PCT/JP2013/078222.
Paliga et al., "Human Amyloid Precursor-like Protein 1 cDNA Cloning, Ectopic Expression in COS-7 Cells and Identification of Soluble Forms in the Cerebrospinal Fluid," Eur. J. Biochem., vol. 250, pp. 354-363, 1997.
Lichtenthaler et al., "A Novel Substrate for Analyzing Alzheimer's Disease g-Secretase," FEBS Letters, vol. 453, pp. 288-292, 1999.
Rohn et al., "A Monoclonal Antibody to Amyloid Precursor Protein Induces Neuronal Apoptosis," Journal of Neurochemistry, vol. 74, pp. 2331-2342, 2000.
Kohler et al., "Continuous Cultures of Fused Cells Secreting Antibody of Predefined Specificity," Nature, vol. 256, pp. 495-497, Aug. 7, 1975.
Henderson et al., "HLA-A2.1-Associated Peptides from a Mutant Cell Line: A Second Pathway of Antigen Presentation," Science, 1992, vol. 255, pp. 1264-1266.
Hage et al., "Preprocalcitonin Signal Peptide Generates a Cytotoxic T Lymphocyte-Defined Tumor Epitope Processed by a Proteasome-Independent Pathway," PNAS, Jul. 2008, vol. 105, No. 29, pp. 10119-10124.
Abbott, "The Plaque Plan," Nature, Nov. 2008, vol. 456, pp. 161-164.
Nikolaev et al., "APP Binds DR6 to Trigger Axon Pruning and Neuron Death via Distinct Caspases," Nature, Feb. 2009, vol. 457, pp. 981-989.
Mar. 13, 2012 International Search Report issued in International Patent Application No. PCT/JP2012/050210.
Jul. 10, 2013 International Preliminary Report on Patentability issued in International Patent Application No. PCT/JP2012/050210.
Harlow et al., Antibodies; A Laboratory Manual, Spring Harbor Laboratory, 1988, Chapter 5, pp. 72-77.
Hopp et al., "Prediction of Protein Antigenic Determinants from Amino Acid Sequences," Proc. Natl. Acad. Sci. USA, 1981, vol. 78, No. 6, pp. 3824-3828.
Hilton et al., "Anti-Peptide Antibody Blocks Peptide Binding to MHC Class I Molecules in the Endoplasmic Reticulum", Journal of Immunology, vol. 166, pp. 3952-3956, 2001.
Pomroy et al., "Solubilization of Hydrophobic Peptides by Reversible Cysteine PEGylation", Biochemical and Biophysical Research Communications, vol. 245, No. 2 , pp. 618-621, 1998.
Boulant et al., "Hepatitis C Virus Core Protein is a Dimeric Alpha-Helical Protein Exhibiting Membrane Protein Features", Journal of Virology, vol. 79, No. 17, pp. 11353-11365,2005.
Extended European Search Report for European Patent Application No. 12731948.1, mailed Jul. 14, 2015.
Slivka et al., "Peptide Probes for Protein Transmembrane Domains" ACS Chem. Biol. 3(7):402-411, 2008.
Almen et al., "Mapping the Human Membrane Proteome: A Majority of the Human Membrane Proteins can be Classified According to Function and Evolutionary Origin" BMC Biology 7:50, 2009 (14 pages).
Tam, "Synthetic Peptide Vaccin Design: Synthesis and Properties of a High-Density Multiple Antigenic Peptide System" Proc. Nat!. Acad. Sci. USA 85:5409-5413, 1988.
Beck et al., "Nucleotide Sequence of the Gene ompA Coding the Outer Membrane Protein 11* of *Escherichia coli* K-12" Nucleic Acids Research 8(13):3011-3027, 1980.
Miraglia et al., "A Novel Five-Transmembrane Hematopoietic Stem Cell Antigen: Isolation, Characterization, and Molecular Cloning" Blood 90(12):5013-5021, 1997.
International Search Report for PCT/JP2012/050136, mailed Feb. 28, 2012.
International Preliminary Report on Patentability for PCT/JP2012/050136, mailed Jul. 18, 2013.
Jul. 22, 2015 Office Action issued in U.S. Appl. No. 14/397,920.
Oct. 27, 2015 Office Action issued in U.S. Appl. No. 14/397,920.
Nov. 12, 2015 Office Action issued in U.S. Appl. No. 13/978,419.
Apr. 23, 2015 Office Action issued in U.S. Appl. No. 13/978,584.
Sep. 3, 2015 Office Action issued in U.S. Appl. No. 13/978,584.
Aug. 14, 2015 Office Action issued in U.S. Appl. No. 13/978,419.
Beck et al. Amyloid precursor protein in guinea pids—complete cDNA seuqence and alternative splicing. Biochim Biphys Acta. Mar. 20, 1997; 1351(1-2):17-21.
Böcker et al. IKK-2 is required for TNF-alpha-induced incasion and proliferation of human mesenchymal stem cells. J Mol Med (berl). Oct. 2008;86(10):1183-92.
Oerum et al. Porcine APP cDNAs: molecular cloning and characterization, expression analysis, chromosomal localization and SNP analysis. Biochim Biophys Acta. Jul. 2006;1759(7):378-84,=. Epub Jul. 14, 2006.
Retinal Diseases, in MeSH Disease, National Center for Biotechnology Information, Bethesda, Maryland, USA [online], [retrieved on Dec. 27, 2015]. Retrieved from the Internet: <URL: http://www.ncbi.nlm.nih.gov/mesh/?term=retinal+diseases&report=Full&format=text>.
Jan. 15, 2016 Office Action Issued in U.S. Appl. No. 14/432,326.
Emmott et al., "Nucleolar targeting: the hub of the matter," EMBO reports, 2009, vol. 10, No. 3, pp. 231-238.
Goyal et al., "Phosphorylation-dependent Regulation of Unique Nuclear and Nucleolar Localization Signals of LIM Kinase 2 in Endothelial Cells," Journal of Biological Chemistry, 2006, vol. 281, No. 35, pp. 25223-25230.
Jul. 19, 2011 International Search Report issued in International Patent Application No. PCT/JP2011/062809.
Jan. 8, 2013 International Preliminary Report on Patentability issued in International Patent Application No. PCT/JP2011/062809.
Berendsen, "A Glimpse of the Holy Grail?," Science, vol. 282, No. 5389, pp. 642-643, Oct. 23, 1998.
Bochkov et al., "Phylogenetic Analysis of Partial S1 and N Gene Sequences of Infections Bronchitis Virus Isolates from Italy Revealed Genetic Diversity and Recombination," Virus Genes, vol. 35, pp. 65-71, 2007.
Boursnell et al., "Sequences of the Nucleocapsid Genes from Two Strains of Avian Infectious Bronchitis Virus," J. Gen. Virol., vol. 66, pp. 573-580, 1985.
Bradley et al., "Limits of Cooperativity in a Structurally Modular Protein: Response of the Notch Ankyrin Domain to Analogous Alanine Substitutions in Each Repeat," J Mol. Biol, vol. 324, pp. 373-386, 2002.
Cserpán et al., "The Mechanism of Nuclear Transport of Natural or Artificial Transport Substrates in Digitonin-Permeabilized Cells," Journal of Cell Science, vol. 108, pp. 1849-1861, 1995.
Eiges et al., "Establishment of Human Embryonic Stem Cell-Transfected Clones Carrying a Marker for Undifferentiated Cells," Current Biology, vol. 11, pp. 514-518, 2001.
Fang et al., "Selection of and Recombination between Minor Variants Lead to the Adaptation of an Avian Coronavirus to Primate Cells," Biochemical and Biophysical Research Communications, vol. 336, pp. 417-423, 2005.

(56) References Cited

OTHER PUBLICATIONS

Futaki et al., "Intracellular Protein Delivery Using Membrane-Permeable Peptides," Seibutsu to Kagaku, vol. 43, No. 10, pp. 649-653, 2005.
Hilton et al., "Twenty Proteins Containg a C-Terminal SOCS Box Form Five Structural Classes," Proc. Natl. Acad. Sci. USA, vol. 95, pp. 114-119, Jan. 1998.
Kamura et al., "The Elongin BC Complex Interacts with the Conserved SOCS-Box Motif Present in Members of the SOCS, Ras, WD-40 Repeat, and Ankyrin Repeat Families," Genes & Development, vol. 12, pp. 3872-3881, 1998.
Kamura et al., "VHL-Box and SOCS-Box Domains Determine Binding Specificity for Cul2-Rbx1 and Cul5-Rbx2 Modules of Ubiquitin Ligases," Genes & Development, vol. 18, pp. 3055-3065, 2004.
Kang et al., "The Precursor of Alzheimer's Disease Amyloid A4 Protein Resembles a Cell-Surface Receptor," Nature, vol. 325, pp. 733-736, Feb. 19, 1987.
Kile et al., "The Suppressors of Cytokine Signalling (SOCS)," Cellular and Molecular Life Sciences, vol. 58, pp. 1627-1635, 2001.
Kobayashi et al., "Nucleolar Localization Signals of LIM Kinase 2 Function as a Cell-Penetrating Peptide," Protein & Peptide Letters, vol. 17, pp. 1480-1488, 2010.
Kwak et al., "Amyloid Precursor Protein Regulates Differentiation of Human Neural Stem Cells," Stem Cells Dev., vol. 15, No. 3, pp. 381-389, 2006.
Liu et al., "Rack1 Competes with HSP90 for Binding to HIF-1? and is Required for O2-Independent and HSP90 Inhibitor-Induced Degradation of HIF-1?," Molecular Cell, vol. 25, pp. 207-217, Jan. 26, 2007.
Liu et al., "Calcineurin Promotes Hypoxia-Inducible Factor 1? Expression by Dephosphorylating RACK1 and Blocking Rack1 Dimerization," Journal of Biological Chemistry, vol. 282, No. 51, pp. 37064-37073, Dec. 21, 2007.
Liu et al., "Rack1 vs. HSP90: Competition for HIF-1? Degradation vs. Stablization," Cell Cycle, vol. 6, No. 6, pp. 656-659, Mar. 15, 2007.
Marutle et al., "Modulation of Human Neural Stem Cell Differentiation in Alzheimer (APP23) Transgenic Mice by Phenserine," Proc. Natl. Acad. USA, vol. 104, No. 30, pp. 12506-12511, Jul. 24, 2007.
NCBI database Accession No. Q1M2X0, p. 1, accessed Nov. 7, 2012.
Ngo et al., "Computational Complexity, Protein Structure Prediction, and the Levinthal Paradox," The Protein Folding Problem and Tertiary Structure Prediction, K. Merz Jr. and S. Le Grand, Eds. pp. 491-494, Birchhuser Bosino 1994.
Pokorska et al., "The Analysis of the Transcriptional Activator PrnA Reveals a Tripartite Nuclear Localisation Sequence," J. Mil. Biol., vol. 298, pp. 585-596, 2000.
Reed et al., "Delineation and Modelling of a Nucleolar Retention Signal in the Coronavirus Nucleocapsid Protein," Traffic, vol. 7, pp. 833-848, 2006.
Rudinger, "Peptide Hormones," JA Parsons, Ed., pp. 1-7, Jun. 1976.
Designing Custom Peptides, www.sigma-genosys.com/peptide_design.asp <http://www.sigma-genosys.com/peptide_design.asp>; Sigma-Genosys, pp. 1-2, accessed Dec. 16, 2004.
Sugaya et al., "Practical Issues in Stem Cell Therapy for Alzheimer's Disease," Curr. Alzheimer Res., vol. 4, No. 4, pp. 370-377, 2007, Abstract only.
Takei et al., "Possible Involvement of a Pertussis Toxin-Sensitive GTP-Binding Protein in Protein Transport into Nuclei Isolated from Rat Liver," J. Biochem., vol. 115, pp. 578-583, 1994.
Voet et al., "Biochemistry," John Wiley & Sons, Inc., pp. 235-241, 1995.
Yu et al., "Selective Assembly of HIV-1 Vif-Cul5-ElonginB-ElonginC E3 Ubiquitin Ligase Complex through a Novel SOCS Box and Upstream Cysteines," Genes & Development, vol. 18, pp. 2867-2872, 2004.
Mar. 1, 2011 European Search Report issued in European Application No. 09 704 366.5.
Dec. 5, 2011 European Office Action issued in European Application No. 09 704 366.5.
Apr. 7, 2009 International Search Report issued in International Application No. PCT/2009/051082.
Jul. 13, 2010 International Search Report issued in International Application No. PCT/JP2010/056510.
Oct. 5, 2010 International Search Report issued in International Patent Application No. PCT/JP2010/062691.
Oct. 5, 2010 International Search Report issued in International Patent Application No. PCT/JP2010/062693.
Jan. 18, 2011 International Search Report issued in International Patent Application No. PCT/JP2010/069165.
Jun. 12, 2012 International Preliminary Report on Patentability and Written Opinion issued in International Patent Application No. PCT/JP2010/069165.
Mar. 29, 2010 International Preliminary Report on Patentability and Written Opinion issued in International Application No. PCT/JP2009/051082.
Aug. 17, 2011 Office Action issued in U.S. Appl. No. 12/864,147.
Sep. 30, 2011 Office Action issued in U.S. Appl. No. 12/864,147.
Mar. 12, 2012 Office Action issued in U.S. Appl. No. 12/864,147.
Nov. 14, 2012 Office Action issued in U.S. Appl. No. 13/386,539.
Nov. 14, 2012 Office Action issued in U.S. Appl. No. 13/386,582.
Jan. 31, 2013 Office Action issued in U.S. Appl. No. 13/258,788.

* cited by examiner

US 9,370,182 B2

ANTIMICROBIAL PEPTIDE AND USE THEREOF

TECHNICAL FIELD

The present invention relates to an antimicrobial oligopeptide or polypeptide (or comprehensively called "antimicrobial peptide" hereinafter) and further relates to a pharmaceutical composition (antimicrobial composition, antimicrobial drug) comprising the antimicrobial peptide.

The present application claims priority based on Japanese Patent Application No. 2012-121256 filed on May 28, 2012, and its entire contents are incorporated herein by reference.

BACKGROUND ART

Antimicrobial peptides generally exhibit broad antimicrobial spectra and are considered unlikely to develop drug-resistant microorganisms. Thus, their expected uses include prevention or treatment of bacterial infections in humans and animals as well as provision of antimicrobial properties to products such as food, etc. To date, many antimicrobial peptides have been isolated from various animals and plants (e.g. Patent Documents 1, 2). There have been reported some synthetic antimicrobial peptides designed and synthesized based on known amino acid sequences whose relevance to antimicrobial activities had never been discussed (Patent Document 3).

CITATION LIST

Patent Literature

[Patent Document 1] Japanese Patent Application Publication No. 2000-63400
[Patent Document 2] Japanese Patent Application Publication No. 2001-186887
[Patent Document 3] WO 03/091429A1
[Patent Document 4] WO 2010/117079A1

Non-Patent Literature

[Non-Patent Document 1] PLoS ONE [online], Vol. 5, Issue 3, 2010, e9505
[Non-Patent Document 2] Trends in CELL BIOLOGY, Vol. 8, 1998, pp. 410-415

SUMMARY OF INVENTION

An objective of the present invention is to provide a novel antimicrobial peptide comprising an artificially designed amino acid sequence different from any antimicrobial peptide that is present as a mature peptide in nature and acts as a physiologically active peptide. Another objective is to provide a composition comprising such an antimicrobial peptide as a primary component.

In earnestly researching antimicrobial oligopeptides and polypeptides exhibiting broad antimicrobial spectra encompassing bacteria and fungi, with an amino acid sequence different from conventional antimicrobial peptides as described in the aforementioned Patent Documents, the present inventors looked into an amino acid sequence constituting the signal peptide of an amyloid precursor protein (APP) which could be also considered as a starting material involved in Alzheimer's disease. Consequently, the inventors have come to find out that a synthetic peptide comprising an amino acid sequence constituting such signal peptide (including both cases where it is an oligopeptide and where it is a polypeptide; the same applies hereinafter) exhibits a broad antimicrobial spectrum. Although some synthetic peptides comprising such amino acid sequences had been known as neural differentiation-inducing peptides (Patent Document 4), the discovery of their antimicrobial activities which are totally unrelated to the neural differentiation-inducing abilities has led to completion of this invention.

It has been proposed that in brain neurons, APP is cleaved by a secretase ($\beta$-secretase, $\gamma$-secretase) to yield an amyloid $\beta$ protein (A$\beta$) consisting of typically 40 or 42 amino acid residues, and aggregation (deposition) of A$\beta$ in the brain causes damages to the neurons, resulting in the onset of Alzheimer's disease (amyloid hypothesis). Rather than A$\beta$ cleaved by a secretase from APP, the present inventors looked into the signal peptide moiety of APP which had been thus far attracting no interest in regard to the amyloid hypothesis, and brought about the present invention.

As described in Non-Patent Document 1, it has been known that A$\beta$ itself shows antimicrobial activity, but it has never been known at all that a synthetic peptide comprising the amino acid sequence constituting the signal peptide of APP exhibits antimicrobial activity. Non-Patent Document 1 does not refer to the signal peptide of APP. Non-Patent Document 2 introducing signal peptides in general does not include any disclosure that suggests antimicrobial activities of the signal peptide, either.

The composition disclosed herein comprises, as an antimicrobial peptide (synthetic peptide) being a primary component, a synthetic peptide comprising an amino acid sequence corresponding to a signal peptide of a protein (precursor) among (1) an amyloid precursor protein (APP); and
(2) two species of amyloid precursor-like protein which are APP analog proteins,
    (2-1) amyloid precursor-like protein 1 (APLP1) and
    (2-2) amyloid precursor-like protein 2 (APLP2).

In other words, the composition provided by the present invention is a pharmaceutical composition comprising an artificially synthesized peptide that has an antimicrobial activity against at least one strain of bacteria or fungi and comprises an amino acid sequence represented by any one of SEQ ID NOs: 1 to 6 or an amino acid sequence formed by substituting, deleting and/or adding one, two or three amino acid residues in/from/to the amino acid sequence, and further comprising at least one species of pharmaceutically acceptable carrier.

The amino acid sequence of SEQ ID NO: 1, MLPGLA-LLLLAAWTARA, constitutes the signal peptide (number of amino acid residues: 17) of human APP.

The amino acid sequence of SEQ ID NO: 2, MLPSLA-LLLLAAWTVRA constitutes the signal peptide (number of amino acid residues: 17) of mouse APP.

The amino acid sequence of SEQ ID NO: 3, MGPASPAARGLSRRPGQPPLPLLL-PLLLLLLRAQPAIG, constitutes the signal peptide (number of amino acid residues: 38) of human APLP1.

The amino acid sequence of SEQ ID NO: 4, MGPTSPAARGQGRRWRPPLPLLL-PLSLLLLRAQLAVG, constitutes the signal peptide (number of amino acid residues: 37) of mouse APLP1.

The amino acid sequence of SEQ ID NO: 5, MAATG-TAAAAATGRLLLLLLLVGLTAPALA, constitutes the signal peptide (number of amino acid residues: 29) of human APLP2.

The amino acid sequence of SEQ ID NO: 6, MAATG-TAAAAATGKLLVLLLLGLTAPAAA, constitutes the signal peptide (number of amino acid residues: 29) of mouse APLP2.

A preferable embodiment of the composition disclosed herein comprises, as the antimicrobial peptide, an antimicrobial peptide comprising the amino acid sequence represented by SEQ ID NO: 3, 4, 5 or 6, or an amino acid sequence formed by substituting, deleting and/or adding one, two or three amino acid residues in/from/to the amino acid sequence.

Preferable examples of the carrier used in preparing the composition include a liquid medium capable of dissolving or dispersing the antimicrobial peptide.

The composition disclosed herein may have a high antimicrobial activity due to the antimicrobial peptide comprising the amino acid sequence corresponding (equivalent) to an aforementioned signal peptide ("AP-signal peptide-related sequence" hereinafter) contained therein as the primary component. Typically, an artificially synthesized peptide comprising an AP-signal peptide-related sequence exhibits a broad antimicrobial spectrum and may have antimicrobial activities against Gram-positive bacteria and Gram-negative bacteria as well as fungi.

In general, the synthetic peptide (i.e. antimicrobial peptide) contained as an antimicrobial ingredient in the composition should just have one set (one repeat) of an AP-signal peptide-related sequence while it is not limited to this. For instance, it may be a peptide where two or three sets of an AP-signal peptide-related sequence are located adjacent to each other.

The antimicrobial peptide may comprise at least one amidated amino acid residue. Amidation of a carboxyl group in an amino acid residue (typically the C-terminal amino acid residue of the peptide chain) may increase the structural stability (e.g. protease resistance) of the antimicrobial peptide.

In the antimicrobial peptide, the peptide chain is preferably constituted with a total of 50 or fewer amino acid residues. Such a short peptide chain can be easily produced by chemical synthesis, facilitating the provision of the antimicrobial peptide (synthetic peptide). The antimicrobial peptide disclosed herein has a short length chain (i.e. it has a relatively low molecular weight). Thus, it can be easily handled to provide a composition suitable for in vivo and/or in vitro use.

The present invention also provides a sterilization method, an antimicrobial method or a disinfection method (the expression can be different depending on the purpose) comprising using a composition (more specifically, an antimicrobial peptide) disclosed herein. For instance, the present invention provides an antimicrobial method for suppressing multiplication of at least one strain of bacteria or fungi present in one of the following objects:
(1) a non-human organism;
(2) a culture tissue or a cell culture removed from an organism including humans, which is to be incubated in vitro; and
(3) a non-biogenic article;
the method comprising supplying a composition disclosed herein (i.e. an antimicrobial peptide disclosed herein) to the object on the surface or internally.

DESCRIPTION OF EMBODIMENTS

Preferred embodiments of the present invention are described below. Note that technical matters other than the matters particularly mentioned in the present description (e.g. primary structures of antimicrobial peptides disclosed herein) which are required for carrying out the present invention (e.g., general matters relating to peptide synthesis, polynucleotide synthesis, and preparation of a composition comprising a peptide) are matters of design variation that could be apprehended by a person skilled in the art based on conventional art in such fields as organic chemistry, biochemistry, genetic engineering, protein engineering, molecular biology, medicine, pharmacology, hygienics and the like. The present invention can be practiced based on the technical details disclosed in the present description and common general technical knowledge in the pertinent fields. In the following description, amino acids are indicated by single-letter designations (in sequence listings, by three-letter designations) in accordance with the nomenclature for amino acids set forth in the IUPAC-IUB guidelines.

In the present description, the "artificially synthesized antimicrobial peptide" is not present by itself as a mature peptide chain in the nature, but refers to a peptide fragment that is manufactured by artificial chemical synthesis or biosynthesis (i.e. genetic engineering-based production).

In this description, the term "antimicrobial peptide" refers to an amino acid polymer having a plurality of peptide bonds that exhibits an antimicrobial activity against at least one strain of bacteria or fungi, and is not limited by the number of amino acid residues contained in the peptide chain. The antimicrobial peptide in this description encompasses an oligopeptide having up to about 20 amino acid residues and also a polypeptide formed with more than 20 amino acid residues.

In this description, unless otherwise specified, the term "amino acid residue" includes the N-terminal amino acid and the C-terminal amino acid of a peptide chain.

In this description, the term "polynucleotide" refers to a polymer (nucleic acids) in which several nucleotides are linked by phosphodiester bonds, but not limited by the number of nucleotides. The polynucleotide in the present description encompasses DNA fragments and RNA fragments of various lengths.

In this description, "an amino acid sequence formed by substituting, deleting and/or adding one, two or three amino acid residues" in/from/to a prescribed amino acid sequence is a typical example of a modified amino acid sequence obtainable by partial modification of the prescribed amino acid sequence without a loss in the antimicrobial activity against at least one strain of bacteria or fungi. Examples of such modified amino acid sequence include a sequence obtainable by so-called conservative amino acid replacement where one to a few (typically one to three) amino acid residues are conservatively replaced (e.g. a sequence wherein a basic amino acid residue has been replaced with another basic amino acid residue, a sequence wherein a hydrophobic amino acid residue has been replaced with another hydrophobic amino acid residue), a sequence such that one or a few (typically about two or three) amino acid residues have been added (inserted) to the prescribed amino acid sequence, a sequence such that one or a few (typically about two or three) amino acid residues have been deleted (removed) from the prescribed amino acid sequence, and the like.

As the AP-signal peptide-related sequence, can be used the amino acid sequence constituting the signal peptide of the APP represented by SEQ ID NO: 1 or 2, or an amino acid sequence modified from this sequence (typical modified amino acid sequences are as described above; the same applies hereinafter). Alternatively, can be used the amino acid sequence constituting the signal peptide of the APLP1 represented by SEQ ID NO: 3 or 4, or an amino acid sequence modified from this sequence; or the amino acid sequence constituting the signal peptide of the APLP2 represented by SEQ ID NO: 5 or 6, or an amino acid sequence modified from this sequence. While it is preferable that all amino acid residues are L-amino acids, as long as the antimicrobial activity is not lost, some or all of the amino acid residues may be replaced with the corresponding D-amino acids.

The chain length (number of amino acid residues) of the antimicrobial peptide disclosed herein may vary depending on the length of the AP-signal peptide-related sequence and thus it is not particularly limited. The total number of amino acid residues is suitably 100 or less, preferably 50 or less, or more preferably 40 or less. No particular limitation is imposed on the conformation (spatial structure) of the peptide as long as the antimicrobial activity is obtained in the use environment. From the standpoint of the less likelihood of becoming an immunogen (antigen), a linear or helical conformation is preferable. Peptides in these conformations are less likely to form epitopes. From such a standpoint, a preferable synthetic peptide has solely one set (one repeat) of an AP-signal peptide-related sequence.

Alternatively, the peptide may have several (typically two or three) sets of the same AP-signal peptide-related sequence or AP-signal peptide-related sequences that are different from each other. For instance, the synthetic peptide may consist of a peptide chain comprising two or three sets of the amino acid sequence represented by one of SEQ ID NOs: 1 to 6 repetitively located from the N-terminus, adjacent to each other. In this embodiment, the synthetic peptide may have a structure such that one repeat of an AP-signal peptide-related sequence is coupled via a short linker sequence (a hinge moiety) to one repeat of another AP-signal peptide-related sequence. Typical examples of such linker sequence include a sequence constituted with about one to nine (e.g. one, two or three) glycine residues and/or serine residues.

As long as the antimicrobial activity is not lost, the antimicrobial peptide disclosed herein may comprise a partial sequence besides the AP-signal peptide-related sequence. In other words, the term "antimicrobial peptide comprising an AP-signal peptide-related sequence", which is the primary component of the composition of this invention, refers to an antimicrobial peptide primarily including an AP-signal peptide-related sequence (typically, consisting essentially of an AP-signal peptide-related sequence), not excluding the presence of a small number of amino acid residues that exert no influence on the manifestation of antimicrobial activity.

Among the antimicrobial peptides disclosed herein, a relatively short peptide chain can be easily manufactured based on general chemical synthesis methodologies. For instance, any of conventional solid-phase and liquid-phase synthetic methods can be employed. A preferable solid-phase synthetic method uses Boc (t-butyloxycarbonyl) or Fmoc (9-fluorenylmethoxycarbonyl) as the protecting group for the amino group. For the antimicrobial peptide, a peptide chain having a desired amino acid sequence and a moiety with a modification (e.g., C-terminal amidation) can be synthesized by solid-phase synthesis using a commercial peptide synthesizer (e.g. available from PerSeptive Biosystems, Applied Biosystems, etc.).

Alternatively, the antimicrobial peptide may be biosynthesized based on genetic engineering techniques. This approach is suitable for producing a relatively long polypeptide chain. In particular, a DNA is synthesized so as to have a nucleotide sequence (including the ATG initiation codon) encoding the amino acid sequence of a desired antimicrobial peptide. Then, in accordance with the host cell line of choice, a recombinant vector is constructed so as to have an expression gene construct formed from the DNA and various regulatory elements (including a promoter, ribosome binding site, terminator, enhancer, and various cis-elements which control the expression level) to allow expression of the amino acid sequence in the host cells.

By an ordinary technique, this recombinant vector is inserted into prescribed host cells (e.g. yeasts, insect cells, plant cells, mammalian cells), and the host cells, or tissue or a mass containing these cells are cultured under specific conditions. In this way, the target polypeptide can be expressed and produced intracellularly. The polypeptide is isolated from the host cells (from the culture medium if the polypeptide is secreted) and purified to obtain the target antimicrobial peptide.

Methods hitherto used in the art may be directly employed without modification for constructing the recombinant vector and introducing the constructed recombinant vector into the host cells. Because such methods themselves are not distinctive to the present invention, detailed description is omitted.

For example, a fusion protein expression system may be employed to allow efficient large-scale production in host cells. In particular, a gene (DNA) coding for the amino acid sequence of the antimicrobial peptide of interest is chemically synthesized, and the synthesized gene is introduced to a preferred site on a suitable fusion protein expression vector (e.g. GST (glutathione S-transferase) fusion protein expression vectors such as the pET series available from Novagen as well as the pGEX series available from Amersham Bioscience). Host cells (typically, *Escherichia coli*) are then transformed by the vector. The resulting transformant is cultured to produce the target fusion protein. This protein is then extracted and purified. Subsequently, the purified fusion protein is cleaved with a specific enzyme (protease), and the cleaved fragments of the target peptide (the designed antimicrobial peptide) are collected by a method such as affinity chromatography. The antimicrobial peptide of the present invention can be produced by using such a heretofore known fusion protein expression system (e.g., the GST/His system available from Amersham Bioscience may be used).

Alternatively, the target polypeptide may be synthesized in vitro by constructing a template DNA for a cell-free protein synthesis system (i.e., a synthesized gene fragment having a nucleotide sequence that codes for the amino acid sequence of the antimicrobial peptide), and employing a cell-free protein synthesis system with use of various compounds (e.g., ATP, RNA polymerase, amino acids, etc.) required for the peptide synthesis. For information concerning cell-free protein synthesis systems, reference may be made to, for example, Shimizu et al., Nature Biotechnology, 19, 751-755 (2001), and Madin et al., Proc. Natl. Acad. Sci. USA, 97(2), 559-564 (2000). Based on the technology described in these articles, many corporations have been conducting contract manufacturing of polypeptides at the time of filing this application. Cell-free protein synthesis kits are commercially available as well.

The antimicrobial peptide disclosed herein is suitable as a primary component in a composition since it has a high antimicrobial activity against at least one strain of bacteria or fungi with a preferable peptide further having a relatively broad antimicrobial spectrum.

A composition comprising such an antimicrobial peptide can be used, for instance, for treatment of bacterial infections, disinfection of wound surfaces, prevention of eye diseases, mouse washing (gargling), preserving or keeping freshness of food, deodorization, antimicrobial treatment (sterilization or microbiostatic treatment) of surfaces of furniture and sanitization units, and so on.

Besides the antimicrobial peptide, the pharmaceutically acceptable carrier that can be contained in the composition may vary depending on the usage or form of the composition. Examples include water and other aqueous solvents, non-aqueous solvents (organic solvents), various fillers, bulking agents, binders, wetting agents, surfactants, excipients, colorants, fragrances and the like.

A liquid medium capable of dissolving or dispersing the antimicrobial peptide is preferable. Since the antimicrobial peptide disclosed herein has a relatively high hydrophobic amino acid residue content, a liquid medium containing a solvent such as DMSO (dimethyl sulfoxide), DMF (dimethylformamide), isopropanol and the like (e.g. a mixed solvent of water and DMSO) can be preferably used.

The form of the composition is not particularly limited. For instance, for an embodiment where the target object is an organism (a human or a non-human animal) (i.e. when used in vivo), or for an embodiment where the target object is a cultured tissue (a culture medium) or a cell culture (a culture medium) that has been removed from an organism including a human and is to be incubated in vitro (i.e. when used in vitro), typical forms of internal drugs or topical agents include ointments, liquid formulas, suspensions, emulsions, aerosols, foams, granules, powders, tablets, capsules and the like. For injection, etc., it may be produced as a freeze-dried product or pellets to prepare a drug solution just prior to use by dissolving or dispersing it in a liquid medium such as suitable saline or suitable buffer (e.g., PBS).

On the other hand, when the target object is a non-biogenic article (typically tableware, furniture and other appliances, clothes, shoes, bags and other personal accessories, sanitization units), examples include liquid formulas, suspensions, emulsions, aerosols, foams and the like. It may be in a form of wet cloth or paper moistened in advance with a liquid-form antimicrobial agent at a prescribed peptide concentration. Using the composition in such a form, a non-biogenic article surface as the target can be provided with antimicrobial treatment.

The process itself of preparing various forms of compositions with the antimicrobial peptide (primary ingredient) and various carriers (secondary ingredients) may be carried out in accordance with a heretofore known method. Because such a preparation process itself is not distinctive to the present invention, detailed description is omitted. The detail information regarding formulations can be found in, for example, Comprehensive Medicinal Chemistry, edited by Corwin Hansch and published by Pergamon Press (1990).

The composition disclosed herein can be used according to a method and dosage appropriate for the form and purpose. For instance, as a liquid formula, it can be administered to a subject person (or a subject animal) by intravenous, intramuscular, subcutaneous, intradermal or intraperitoneal injection, or through an enema. Alternatively, a solid formulation such as a tablet can be orally administered. For instance, to cancer patients on radiation therapy or AIDS patients, prevention and treatment of bacterial infections are of great interest. A composition comprising an antimicrobial peptide disclosed herein may exhibit a high antimicrobial activity against bacteria (e.g. S. aureus) that can cause infections.

When used on a non-human object, for example, when used for antimicrobial treatment of sanitary pottery surfaces or antimicrobial treatment (preservation) of food, a liquid formula containing a relatively large amount (e.g. 1 mg/mL to 100 mg/mL) of the antimicrobial peptide can be directly sprayed onto the object surface, or the object surface can be wiped with wet cloth or paper moistened with the liquid formula. These are merely examples. The same forms and usages as conventional agricultural chemicals, quasi-drugs and the like containing peptide-based antibiotics or peptides as ingredients can be applied.

A polynucleotide coding for an antimicrobial peptide of the present invention can be used as a material for so-called gene therapy. For instance, by inserting a gene (typically a DNA segment or an RNA segment) coding for the antimicrobial peptide into a suitable vector and introducing the vector to a target cite, the antimicrobial peptide according to the present invention can be regularly expressed in the organism (cells). Accordingly, a polynucleotide (DNA segment, RNA segment, etc.) coding for an antimicrobial peptide of the present invention is useful as a drug to prevent or treat bacterial infections in the patients described above.

In the field of regenerative medicines, it is important to prevent bacterial infections during incubation of skin, bone and various organs. The antimicrobial peptide disclosed herein may exhibit extremely low toxicity to mammalian cells and tissue while exhibiting selective antimicrobial activities against bacteria. Thus, it is especially useful as a drug to prevent bacterial infections in cultured organs, etc. For example, as shown in the worked examples described later, an antimicrobial peptide of the present invention comprising an AP-signal peptide-related sequence can be added to a culture medium, by itself or as a composition containing the peptide as a primary component, to prevent bacterial infections in the organ being cultured and the like.

For a cultured tissue or a cell culture, a polynucleotide coding for an antimicrobial peptide disclosed herein can be used as a gene therapy material. For instance, by inserting a gene (typically a DNA segment or an RNA segment) coding for an antimicrobial peptide of the present invention into a suitable vector and introducing the vector to the target cultured tissue (i.e. cells), the antimicrobial peptide according to the present invention can be expressed in the cultured tissue (cells) regularly or at desired timing. Accordingly, a polynucleotide (DNA segment, RNA segment, etc.) coding for an antimicrobial peptide disclosed herein is useful as a drug to prevent bacterial infections in a cultured tissue.

Several worked examples relating to the present invention are described below while these examples are not intended to limit the scope of the invention.

<Experiment 1: Peptide Synthesis>

A total of 8 different synthetic peptides (Samples 1 to 6, Comparative Samples 7 and 8) were produced, using a peptide synthesizer described later. Table 1 lists the amino acid sequences of these synthetic peptides.

TABLE 1

| Sample No. | Amino acid sequence | Total number of amino acid residues |
|---|---|---|
| 1 | MLPGLALLLLAAWTARA (SEQ ID NO: 1) | 17 |
| 2 | MLPSLALLLLAAWTVRA (SEQ ID NO: 2) | 17 |
| 3 | MGPASPAARGLSRRPGQPPLPLLLLPLLLLLLRAQPAIG (SEQ ID NO: 3) | 38 |
| 4 | MGPTSPAARGQGRRWRPPLPLLLPLSLLLLRAQLAVG (SEQ ID NO: 4) | 37 |
| 5 | MAATGTAAAAATGRLLLLLLVGLTAPALA (SEQ ID NO: 5) | 29 |
| 6 | MAATGTAAAAATGKLLVLLLLGLTAPAAA (SEQ ID NO: 6) | 29 |
| 7 | TLHQQCIRVLKNNID (SEQ ID NO: 7) | 15 |
| 8 | DYEDRYYRENMHRYPNQVYYRPMDEYSNQNNFVHDC (SEQ ID NO: 8) | 36 |

As shown in Table 1, Samples 1 to 6 are peptides comprising the AP-signal peptide-related sequences corresponding to SEQ ID NOs: 1 to 6, respectively. On the other hand, Samples 7 and 8 are synthetic peptides comprising amino acid sequences (15 amino acid residues and 36 amino acid residues, respectively) not related at all to AP-signal peptide-related sequences.

All peptides were synthesized by solid-phase synthesis (Fmoc chemistry) using a commercial peptide synthesizer (available from Intavis AG) according to the operation manual and purified by high performance liquid chromatography (Waters 600, available from Waters). Because the synthetic peptide production and purification processes themselves are merely conventional techniques, but not features that characterize the present invention, detailed description is omitted.

Each sample synthesized was dissolved in 10% DMSO in distilled water (sterile) to prepare a stock solution having a peptide concentration of 1 mM.

<Experiment 2: Antimicrobial Activities of Synthetic Peptides>

With respect to the peptides (Samples 1 to 8) synthesized in Experiment 1, using an *S. aureus* (209P) as a Gram-positive bacterium, an *E. coli* (NIH-JC2) as a Gram-negative bacterium as well as a *C. albicans* (NBRC-1594) as a fungus, antimicrobial activities (minimum inhibitory concentrations, MICs) were analyzed against these microorganisms.

The two bacterial strains (*S. aureus*, *E. coli*) were subcultured from storage media to agar plate media ("Mueller Hinton Agar" available from DIFCO), then inoculated into liquid media ("Mueller Hinton broth II" available from DIFCO) and cultured at 30° C. or 37° C. for 24 hours. Subsequently, the aforementioned medium was added to the culture media to dilute and prepare inocula at bacterial concentrations of $2 \times 10^5$ cells/mL.

On the other hand, with respect to the one fungus strain (*C. albicans*), the surface of a slant culture was washed with a physiological saline containing 0.1% Tween® 80 to prepare a conidial suspension. The suspension was filtered with a Falcon® cell strainer and diluted with a MOPS-buffered RPMI1640 medium to prepare an inoculum at a fungus concentration of $2 \times 10^4$ cells/mL.

Antimicrobial activity tests were conducted as follows. First, the respective peptides (Samples 1 to 8) were diluted with sterile distilled water to prepare drug (synthetic peptide) solutions having maximum test concentrations of about 256 μM, and further diluted with sterile distilled water to prepare two-fold serial dilutions of the drug solutions (peptide concentrations: 256 μM, 128 μM, 64 μM, 32 μM, 16 μM, 8 μM, 4 μM, 2 μM and 1 μM) for the sample peptides, respectively.

The peptide-containing solutions prepared to the respective concentrations were aliquoted into 96-well microplates at 20 μL per well. In test sections against the fungus, 80 μL of the MOPS-buffered RPMI1640 medium was added to each well. In test sections against the bacteria, 80 μL of the liquid medium (Mueller Hinton broth II) was added to each well.

Subsequently, 100 μL of one of the inocula was added to each well and incubation was started in an incubator at 30° C. or 37° C. After 24 hours, the multiplication (growth) of the microorganisms was analyzed by measurements of turbidity ($OD_{600}$). The minimum drug concentration (peptide concentration) at which no turbidity increase was observed upon the measurement was set as the MIC (unit: μM) in this experiment. The results are shown in Table 2.

[Table 2]

TABLE 2

| Sample | Antimicrobial activities (MIC in μM) | | |
|---|---|---|---|
| No. | *S. aureus* | *E. coli* | *C. albicans* |
| 1 | 16 | 32 | 32 |
| 2 | 16 | 32 | 32 |
| 3 | 4 | 16 | 16 |
| 4 | 4 | 16 | 16 |
| 5 | 8 | 16 | 16 |
| 6 | 8 | 16 | 16 |
| 7 | >256 | >256 | >256 |
| 8 | >256 | >256 | >256 |

As evident from the results shown in Table 2, the synthetic peptides (Samples 1 to 6) comprising AP-signal peptide-related sequences all exhibited high antimicrobial activities against all microorganism strains. On the other hand, with respect to the comparative synthetic peptides (Samples 7, 8) comprising the amino acid sequences unrelated to AP-signal peptide-related sequences, no antimicrobial activities were observed against any microorganism strain.

<Experiment 3: Preparation of Granular Formulation>

50 mg of the synthetic peptide of Sample 1 was mixed with 50 mg of crystallized cellulose and 400 mg of lactose. 1 mL of an ethanol-water mixture was added thereto and the resultant was kneaded well. The resulting mixture was prepared into granules according to a conventional method to obtain a granular composition (granular formulation) comprising the antimicrobial peptide as the primary ingredient.

INDUSTRIAL APPLICABILITY

As described above, the antimicrobial peptide of this invention has a high antimicrobial activity; and therefore, it can be used, for instance, as a medicine or hygienic material. Thus, it can be used as a peptide ingredient for medicines.

[Sequence Listing Free Text]

SEQ ID NO: 1 to SEQ ID NO: 8 synthetic peptides

[Sequence Listing]

TG13-001PCT ST25.txt

The invention claimed is:

1. A pharmaceutical composition comprising:
   at least 4 µM of an artificially synthesized peptide that has an antimicrobial activity against at least one strain of bacteria or fungi; and
   a pharmaceutically acceptable carrier;
   wherein the artificially synthesized peptide consists of an amino acid sequence represented by any one of SEQ ID NOs: 3 to 6.

2. The pharmaceutical composition according to claim 1, wherein the pharmaceutically acceptable carrier comprises a liquid medium, and the artificially synthesized peptide is dissolved in or dispersed throughout the liquid medium.

3. A method for suppressing multiplication of at least one strain of bacteria or fungi, the method comprising supplying the pharmaceutical composition according to claim 1 to one of the following objects:
   (1) a non-human organism;
   (2) an in vitro cultured tissue or cell isolated from an organism selected from the group consisting of human and non-human animal; and
   (3) a non-biogenic article.

* * * * *

SEQUENCE LISTING

<160> NUMBER OF SEQ ID NOS: 8

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Met Leu Pro Gly Leu Ala Leu Leu Leu Leu Ala Ala Trp Thr Ala Arg
1               5                   10                  15

Ala

```
<210> SEQ ID NO 2
<211> LENGTH: 17
<212> TYPE: PRT
<213> ORGANISM: Artificial Sequence
<220> FEATURE:
<223> OTHER INFORMATION: Synthetic peptide

<400> SEQUENCE: 2

Met Leu Pro Ser Leu Ala Leu Leu Leu Ala Ala Trp Thr Val Arg
1               5                   10                  15

Ala

<210> SEQ ID NO 3
<211> LENGTH: 38
<212> TYPE: PRT
<213> ORGANISM: Artificial Sequence
<220> FEATURE:
<223> OTHER INFORMATION: Synthetic peptide

<400> SEQUENCE: 3

Met Gly Pro Ala Ser Pro Ala Ala Arg Gly Leu Ser Arg Arg Pro Gly
1               5                   10                  15

Gln Pro Pro Leu Pro Leu Leu Leu Pro Leu Leu Leu Leu Leu Arg
            20                  25                  30

Ala Gln Pro Ala Ile Gly
        35

<210> SEQ ID NO 4
<211> LENGTH: 37
<212> TYPE: PRT
<213> ORGANISM: Artificial Sequence
<220> FEATURE:
<223> OTHER INFORMATION: Synthetic peptide

<400> SEQUENCE: 4

Met Gly Pro Thr Ser Pro Ala Ala Arg Gly Gln Gly Arg Arg Trp Arg
1               5                   10                  15

Pro Pro Leu Pro Leu Leu Leu Pro Leu Ser Leu Leu Leu Arg Ala
            20                  25                  30

Gln Leu Ala Val Gly
        35

<210> SEQ ID NO 5
<211> LENGTH: 29
<212> TYPE: PRT
<213> ORGANISM: Artificial Sequence
<220> FEATURE:
<223> OTHER INFORMATION: Synthetic peptide

<400> SEQUENCE: 5

Met Ala Ala Thr Gly Thr Ala Ala Ala Ala Thr Gly Arg Leu Leu
1               5                   10                  15

Leu Leu Leu Leu Val Gly Leu Thr Ala Pro Ala Leu Ala
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic peptide

<400> SEQUENCE: 6
```

```
Met Ala Ala Thr Gly Thr Ala Ala Ala Ala Thr Gly Lys Leu Leu
1               5                   10                  15

Val Leu Leu Leu Leu Gly Leu Thr Ala Pro Ala Ala Ala
            20                  25

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Thr Leu His Gln Gln Cys Ile Arg Val Leu Lys Asn Asn Ile Asp
1               5                   10                  15

<210> SEQ ID NO 8
<211> LENGTH: 36
<212> TYPE: PRT
<213> ORGANISM: Artificial Sequence
<220> FEATURE:
<223> OTHER INFORMATION: Synthetic peptide

<400> SEQUENCE: 8

Asp Tyr Glu Asp Arg Tyr Tyr Arg Glu Asn Met His Arg Tyr Pro Asn
1               5                   10                  15

Gln Val Tyr Tyr Arg Pro Met Asp Glu Tyr Ser Asn Gln Asn Asn Phe
            20                  25                  30

Val His Asp Cys
        35
```